(12) United States Patent
Castellini

(10) Patent No.: US 6,482,006 B2
(45) Date of Patent: Nov. 19, 2002

(54) UNIT FOR DETECTING CONTAMINATING AGENTS, ESPECIALLY IN DENTAL SURGERIES, AND A DENTAL UNIT EQUIPPED WITH SUCH A DETECTING UNIT

(75) Inventor: Franco Castellini, Bologna (IT)

(73) Assignee: Castellini S.p.A., Bologna (IL)

( * ) Notice: Subject to any disclaimer, the term of this patent is extended or adjusted under 35 U.S.C. 154(b) by 0 days.

(21) Appl. No.: 09/880,426

(22) Filed: Jun. 13, 2001

(65) Prior Publication Data

US 2001/0041323 A1 Nov. 15, 2001

(51) Int. Cl.[7] ............................................. A61C 17/00
(52) U.S. Cl. .................................... 433/80; 422/105
(58) Field of Search .................... 433/84, 91, 95, 433/80; 422/105

(56) References Cited

U.S. PATENT DOCUMENTS

| | | | |
|---|---|---|---|
| 4,545,956 A | * 10/1985 | Ciszewski et al. | ............ 422/28 |
| 4,764,114 A | 8/1988 | Jeffcoat et al. | |
| 5,558,841 A | * 9/1996 | Nakagawa et al. | ......... 422/105 |
| 5,785,523 A | * 7/1998 | Overmyer | .................... 433/82 |
| 5,837,204 A | * 11/1998 | Prevost et al. | ............. 422/105 |
| 6,106,771 A | * 8/2000 | Fitton | .......................... 422/14 |

FOREIGN PATENT DOCUMENTS

| | | |
|---|---|---|
| DE | 196 33 808 A1 | 2/1998 |
| EP | 0 903 180 A2 | 3/1999 |
| EP | 0 990 900 A2 | 4/2000 |
| EP | 0 304 871 A2 | 3/2001 |
| JP | 274654 | 10/2000 |
| WO | WO 94/04078 | 3/1994 |
| WO | WO 00/72019 A2 | 11/2000 |

OTHER PUBLICATIONS

European Search Report; Dec. 11, 2001 from corresponding application EP 01 387.

* cited by examiner

*Primary Examiner*—Ralph A. Lewis
(74) *Attorney, Agent, or Firm*—Fay, Sharpe, Fagan, Minnich & McKee, LLP

(57) ABSTRACT

A unit for detecting contaminating agents, especially in dental surgeries, comprises detecting-transducing means of a chemical, biochemical or electrical type designed to detect a quantity as a function of a variable to be checked and to provide an electrical signal corresponding to the quantity detected; and means for signaling the quantity, connected to the detecting-transducing means.

21 Claims, 1 Drawing Sheet

US 6,482,006 B2

UNIT FOR DETECTING CONTAMINATING AGENTS, ESPECIALLY IN DENTAL SURGERIES, AND A DENTAL UNIT EQUIPPED WITH SUCH A DETECTING UNIT

BACKGROUND OF THE INVENTION

The present invention relates to a unit for detecting contaminating agents, such as bacterial loads in user fluids and biological and chemical indicators in fluids drawn from a patient undergoing treatment in a dental surgery. The invention also relates to a dental unit equipped with such a detecting unit.

The invention addresses dental surgeries in particular. In dental surgeries, dental units of the latest generation are of extremely high quality in terms of functionality, appliance control and, above all, level of sterility. This high quality is the result of constant research and development of solutions for the improvement of dental units which, in the philosophy of the Applicant, means also being able to offer health-care providers and patients an effective means of detecting biological indicators of diseases that can be transmitted during a dental treatment where there is a high risk of cross-infection between patient, health-care provider and dental unit. This risk applies to the dental surgery as a whole and to all the equipment normally used in it.

The ultimate goal of manufacturers of medical and dental equipment is to provide solutions capable of allowing treatment to be carried out under conditions of total safety for both health-care providers and patients. It is in this perspective that we must view the development of recent devices for disinfecting/sterilizing dental handpieces and dental unit water and air lines (even between successive patient treatments) and the use of disposable instruments.

There is growing awareness, among health-care providers, not only of the risks of transmitting certain types of diseases during dental treatment, for example by direct contact with blood, but also of the dangers of infection due to the presence of bacteria in the user fluids of a dental unit.

SUMMARY OF THE INVENTION

Therefore, in order to ascertain the presence of bacteria in dental unit fluid supply lines and to identify chemical and biological indicators in patients undergoing treatment (thus guaranteeing both patients and health-care providers against the risks of cross infection during successive patient treatments with a contaminated dental unit) the Applicant has designed and developed a total safety unit capable, even in real time, of detecting not only bacteria in the fluids used in a dental unit but also biological and/or chemical indicators in a patient being treated.

Another aim is to provide a dental unit equipped with detecting units of this kind both on the lines that supply the user fluids to the equipment used on a patient, and on the conduits used to aspirate fluids from the patient.

Accordingly, the present invention provides a unit for detecting contaminating agents, especially in dental surgeries, said unit comprising detecting-transducing means of a chemical, biochemical or electrical type designed to detect a quantity as a function of a variable to be checked and to provide an electrical signal corresponding to the quantity detected; and means for signaling the quantity, connected to the detecting-transducing means.

The present invention also provides a dental unit of the type comprising at least one main conduit for supplying a user fluid to a plurality of branches which supply the fluid to a set of handpieces and to patient-user units and a second conduit for aspirating a fluid from a patient; the dental unit comprising as built-in parts of it, detecting-transducing means of a chemical, biochemical or electrical type designed to detect a quantity as a function of a variable to be checked in the user fluid and/or in the fluid aspirated from the patient and to provide an electrical signal corresponding to the quantity detected; and means for signaling the quantity, connected to the detecting-transducing means.

BRIEF DESCRIPTION OF THE DRAWINGS

The technical features of the present invention, in accordance with the above-mentioned aims, are set out in the claims below and the advantages more clearly illustrated in the detailed description which follows, with reference to the accompanying drawings, which illustrate a preferred embodiment of the invention without restricting the scope of the inventive concept, and in which:

DESCRIPTION OF THE PREFERRED EMBODIMENTS

Figure 1:
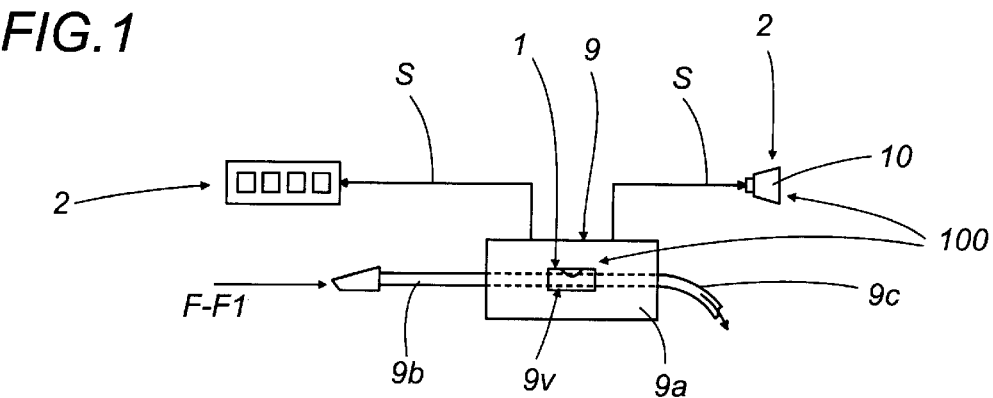
FIG. 1 is a schematic side view of a detecting unit according to the present invention, applied to an independent aspirator.

With reference to the accompanying drawings, in particular FIG. 1, the numeral 100 denotes in its entirety the unit according to the present invention, designed in particular to detect contaminating agents in a dental surgery.

The unit basically comprises detecting-transducing means 1 which may be of a chemical, biochemical or electrical type and are designed to detect a quantity as a function of a variable to be checked and to provide an electrical signal S corresponding to the quantity detected.

The variables may therefore differ according to the task for which the means 1 are to be used; for example, to detect the presence of variables such as bacterial loads in user fluids F used on dental units, or biological agents, specific antibodies, viruses, and biological, chemical, or biochemical factors in fluids F1 drawn from a patient, usually consisting of the patient's blood and saliva.

Connected to the detecting-transducing means 1 there are means 2 for signaling the quantity detected, which, as described below, may differ according to the requirements of the dental surgery.

In a first simplified version described here purely by way of example without limiting the scope of the invention, the unit 100 may consist of an independent aspirating unit 9 which comprises a casing 9a, a suction and receiving portion 9b and an outlet portion 9c, and to which the detecting-transducing means 1 and the signaling means 2 are connected. The aspirating unit 9 may suck in the fluid F from the main water conduit of a dental unit or, alternatively, may aspirate the fluid F1 from the patient.

Obviously, the detecting-transducing means 1 in the aspirating unit 9 differ according to the variables to be detected. Thus, the fluid to be checked may be drawn into an appropriate tank 9V equipped with the sensors 1, or the fluid may be allowed to flow for a preset time through an area where the sensor 1 comes into contact with the fluid.

Constructionally, the detecting-transducing means 1 may consist of a sensor such as an electrode or a bio-sensor (illustrated schematically in the drawings) which is connected to the signaling means 2 and which can be set according to the variable to be detected, or which, alternatively, in combination with the parameters of the variable, may be preset according to a defined threshold.

These quantities, which are provided by way of example and differ according to the variables to be detected, may be brought to the attention of the operator in the surgery through the signaling means 2 which may differ according to the type of aspirating unit 9, the variable to be detected or even the requirements or personal preferences of the operator in the dental surgery.

The signaling means 2 may comprise an audible warning element 10 activated by the aforementioned electrical signal S upon detection of the quantity by the detecting-transducing means 1.

Alternatively, the signaling means 2 may comprise a unit 11 for displaying the quantity detected and being again activated by the electrical signal S issued by the detecting-transducing means 1 upon detection of the quantity.

Figure 2:
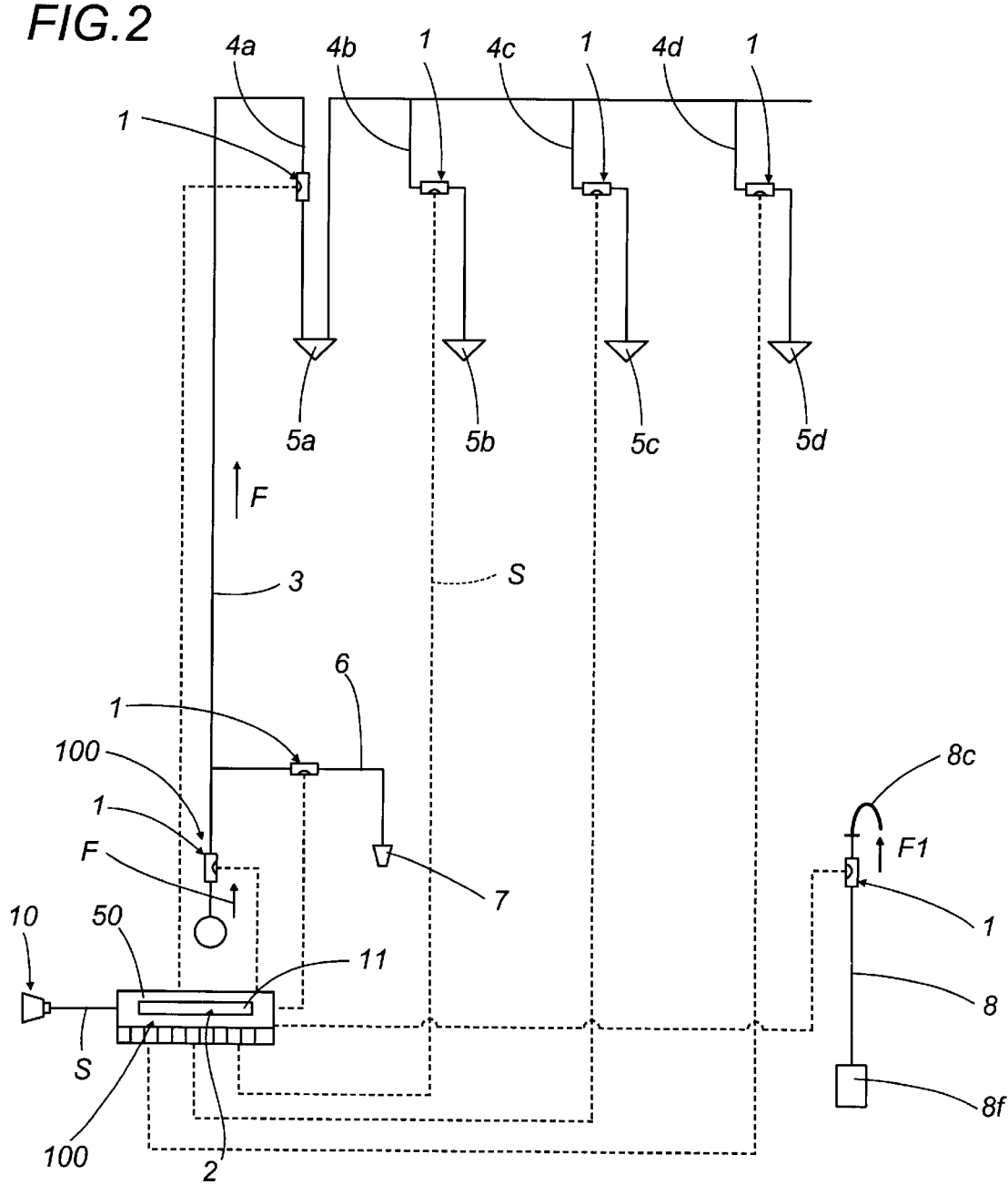
FIG. 2 is a diagram showing the water and air system of a dental unit equipped with the detecting unit according to the present invention.

In another embodiment, illustrated in FIG. 2, especially suitable for on-line detection of contaminant variables in the dental surgery, the unit 100 may be built into a dental unit of known type (again see FIG. 2) comprising at least one main conduit 3 for supplying a user fluid F (water or physiological saline) to a plurality of branches 4a, 4b, 4c, 4d used to supply a set of handpieces 5a, 5b, 5c, 5d and a branch 6 used to supply patient-user units 7 (such as a tumbler). In addition to the user fluid F supply conduits 3, 4 and 6, the dental unit is equipped with a second conduit 8 for aspirating fluids F1 from a patient (this conduit usually being equipped with a cannula 8c and a vacuum source 8f).

The detecting-transducing means 1 may be installed on the main conduit 3 of the dental unit and designed to come into contact with the user fluid F in order, for example, to detect in real time the bacterial load present in the user fluid F.

Moreover, the means 1 may obviously be positioned at critical points most affected by the bacterial loads: for this purpose, the detecting sensors 1 may also be installed on one or more of the branches 4a, 4b, 4c, 4d supplied by the main conduit 3, as well as on the branch 6 that supplies the patient-user units 7 so as to keep possible infections in the user fluid F under control throughout the dental unit.

The variables relating to the patient may be controlled in a similar manner by installing a sensor on the second aspirating conduit 8 to come into contact with the fluid F1 aspirated from the patient so as to detect one or more of the aforementioned variables.

In this case, the means 2 for signaling the quantity detected may consist of a conventional audible or visual warning system installed on the dental unit and usually controlled by a microprocessor unit 50 (as shown in FIG. 2).

The detection unit described above and the dental unit equipped with units of this kind thus achieve the above mentioned aims thanks to a simple but effective structure for checking the user fluids in the dental unit and the fluids from the patient. This check permits the detection in real time of bacterial loads or of external agents potentially capable of contaminating the dental surgery, in particular the dental unit, and of infecting patients and health-care providers.

The above is possible through the simple application of sensors set up to perform the checks required.

The invention described can be subject to numerous modifications and variations without thereby departing from the scope of the inventive concept. Moreover, all the details of the invention may be substituted by technically equivalent elements.

What is claimed is:

1. A unit for detecting contaminating agents, in dental surgeries, comprising:
   detecting-transducing means of a chemical, biochemical or electrical type operatively associated to at least one main conduit of a dental unit, for supplying a user fluid to a plurality of branches which supply the fluid to a set of handpieces, the detecting-transducing means being designed to detect a quantity as a function of biological, chemical and biochemical factors to be checked and to provide an electrical signal corresponding to the quantity detected;
   means for signaling the quantity detected, connected to the detecting-transducing means.

2. The unit according to claim 1, wherein the detecting-transducing means comprises at least one sensor to be connected to the main conduit and designed to come into contact with the user fluid.

3. The unit according to claim 1, wherein the detecting-transducing means comprises at least one sensor to be connected to at least one of the branches supplied by the main conduit.

4. The unit according to claim 3, wherein the detecting-transducing means comprises at least one sensor to be connected to each of the branches supplied by the main conduit.

5. The unit according to claim 1, wherein the unit for detecting contaminating agents is also designed for supplying a user fluid to a branch which supplies the fluid to patient-user units, the detecting-transducing means comprising at least one sensor to be connected to the branch that supplies the patient-user units.

6. The unit according to claim 1, wherein the unit for detecting contaminating agents is also operatively associated to at least one second conduit for aspirating fluids from a patient, the detecting-transducing means comprising at least one sensor to be connected to the second aspirating conduit and being designed to come into contact with the fluid aspirated from the patient.

7. The unit according to claim 1, wherein the detecting-transducing means and the signaling means are connected to an independent unit that sucks in a fluid supplied by a main conduit from a dental unit.

8. The unit according to claim 1, wherein the detecting-transducing means and the signaling means are connected to an independent unit for aspirating a fluid from a patient.

9. The unit according to claim 1, wherein the detecting-transducing means comprises an electrode connected to the signaling means and set according to the variable to be connected.

10. The unit according to claim 1, wherein the detecting-transducing means comprises a bio-sensor connected to the signaling means and set according to the variable to be detected.

11. The unit according to claim 1, wherein the detecting means comprises an electrode connected to the signaling means and preset according to a defined threshold.

12. The unit according to claim 1, wherein the detecting-transducing means comprises a bio-sensor connected to the signaling means and preset according to a defined threshold.

13. The unit according to claim 1, wherein the signaling means comprises an audible warning element activated by the aforementioned electrical signal upon detection of the quantity by the detecting-transducing means.

14. The unit according to claim 1, wherein the signaling means comprises a unit for displaying the quantity detected and activated by the electrical signal upon detection of the quantity by the detecting-transducing means.

15. A dental unit comprising:
   at least one main conduit for supplying a user fluid to a plurality of branches which supply the fluid to a set of handpieces and to patient-user units;
   detecting-transducing means of a chemical, biochemical or electrical type designed to detect a quantity as a function of a variable to be detected in the user fluid and to provide an electrical signal corresponding to the quantity detected;
   means for signaling the quantity detected, connected to the detecting-transducing means.

16. The dental unit according to claim 15, wherein the dental unit further comprises at least one second conduit for aspirating a fluid from a patient undergoing treatment, the detecting-transducing means being designed to operate on the fluid aspirated from a patient and to provide an electrical signal corresponding to the quantity detected.

17. The dental unit according to claim 15, wherein the detecting-transducing means is connected to the main conduit upstream of the branches that supply the handpieces and the patient-user units.

18. The dental unit according to claim 15, wherein the detecting-transducing means is connected to at least one of the branches that supply the hand pieces.

19. The dental unit according to claim 15, wherein the detecting-transducing means is connected to each of the branches that supplies a corresponding handpiece.

20. The dental unit according to claim 15, wherein the detecting-transducing means is connected to the branch that supplies the patient-user units.

21. An apparatus for use during dental procedures for detecting contaminants in fluid supplied to a patient during the dental procedure, said apparatus comprising:
   a conduit for supplying fluid to a patient during a dental procedure;
   contaminant detecting-transducing means operatively associated with said conduit for detecting a quantity of a contaminant in fluid supplied to a patient during a dental procedure through said conduit, said contaminant detecting-transducing means detecting a quantity of contaminant in said fluid as a function of at least one of biological, chemical and biochemical factors and providing an electrical output signal during said dental procedure based upon said quantity of contaminant detected in said fluid being supplied to a patient;
   means for signaling operatively coupled to said contaminant detecting-transducing means, said means for signaling providing an output signal to a person performing the dental procedure during the dental procedure to provide the person performing the dental procedure with information concerning the quantity of contaminant detected in said fluid being supplied to the patient.

* * * * *